United States Patent [19]

Matsumura et al.

[11] 4,333,933

[45] Jun. 8, 1982

[54] BENZOGUANAMINE DERIVATIVES, THEIR PRODUCTION AND PHARMACEUTICAL COMPOSITIONS CONTAINING THE SAME

[75] Inventors: Shingo Matsumura; Hiroshi Enomoto; Yoshiaki Aoyagi; Yoshihisa Shibata, all of Kyoto, Japan

[73] Assignee: Nippon Shinyaku Co., Ltd., Japan

[21] Appl. No.: 266,483

[22] Filed: May 22, 1981

[30] Foreign Application Priority Data

Jun. 4, 1980 [JP] Japan ................................ 55/75875

[51] Int. Cl.$^3$ ................. C07D 251/48; C07D 401/12; A61K 31/44; A61K 31/53
[52] U.S. Cl. ..................................... 424/249; 544/207
[58] Field of Search ..................... 544/207; 424/249

[56] References Cited

U.S. PATENT DOCUMENTS 4,291,162   9/1981   Matsumura et al. ............... 424/249

Primary Examiner—John M. Ford
Attorney, Agent, or Firm—Jacobs & Jacobs

[57] ABSTRACT

Novel 2-amino-4-nicotinoylamino-6-halogenophenyl-s-triazines and acid addition salts thereof, possessing strong anti-inflammatory action when the phenyl group is mono- or di-halogen substituted. The compounds are formulated into pharmaceutical compositions in bulk or dosage form, and are administered to humans and animals having inflammatory conditions or disorders until the same are reduced or overcome. The novel compounds are prepared by various procedures such as reacting a benzoguanamine which is halogen-substituted with an active derivative of nicotinic acid, and recovering the 2-amino-4-nicotinoylamino-6-halogenophenyl-s-triazines thus formed.

20 Claims, No Drawings

BENZOGUANAMINE DERIVATIVES, THEIR PRODUCTION AND PHARMACEUTICAL COMPOSITIONS CONTAINING THE SAME

The present invention relates to benzoguanamine derivatives, their method of production, anti-inflammatory pharmaceutical compositions containing the same and the administration of such compositions to human and animal hosts in need thereof to combat inflammations.

BACKGROUND OF THE INVENTION

2-Amino-4-nicotinoyl-6-phenyl-s-triazines have been found to exhibit marked pharmacological action as set forth in our Japanese application No. Sho-51-34949 as a result of our research and study of various s-triazine derivatives from a chemical and pharmacological point of view.

DESCRIPTION OF THE INVENTION

According to the present invention, we have now discovered novel 2-amino-4-nicotinoylamino-6-halogenophenyl-s-triazines and acid addition salts thereof, which possess strong, anti-inflammatory action when the phenyl group is mono- or dihalogen substituted. Furthermore, we have found synthetic methods for preparing them which is advantageous from an industrial and production point of view. Our invention also comprises anti-inflammatory, pharmaceutical compositions in bulk or dosage form containing effective anti-inflammatory amounts of one or more of said novel compounds, or pharmaceutically acceptable acid addition salts thereof, and the usual or conventional excipients or carriers, as well as the administration of said compositions to humans and animals suffering from inflammatory conditions or disorders.

Examples of novel N-nicotinoylhalogenobenzoguanamines according to the invention are listed below:

TABLE 1

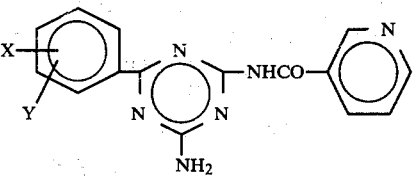

(1)

| Compound Numbers | X and Y | Melting Points (°C.) |
|---|---|---|
| 1 | 4-Chloro | 266–268 |
| 2 | 3-Chloro | 260–262 |
| 3 | 2-Chloro | 224–226 |
| 4 | 4-Bromo | 259–263 |
| 5 | 3-Bromo | 240–243 |
| 6 | 2-Bromo | 233–236 |
| 7 | 4-Iodo | 219–221 |
| 8 | 3-Iodo | 201–204 |
| 9 | 2-Iodo | 125–127 |
| 10 | 4-Fluoro | 257–260 |
| 11 | 3-Fluoro | 222–225 |
| 12 | 2-Fluoro | 233–235 |
| 13 | 3,4-Dichloro | 276–279 |
| 14 | 2,4-Dichloro | 250–252 |
| 15 | 2,5-Dichloro | 239–241 |
| 16 | 3,5-Dichloro | 261–264 |
| 17 | 2,6-Dichloro | 207–210 |
| 18 | 2,3-Dichloro | 211–214 |
| 19 | 2-Fluoro-5-chloro | 255–257 |
| 20 | 2-Fluoro-4-chloro | 249–251 |
| 21 | 2,5-Dibromo | 240–243 |

TABLE 1-continued

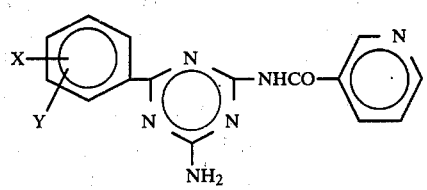

(1)

| Compound Numbers | X and Y | Melting Points (°C.) |
|---|---|---|
| 22 | 2-Bromo-5-chloro | 250–253 |
| 23 | 2-Fluoro-5-bromo | 233–236 |
| 24 | 2-Chloro-5-fluoro | 215–217 |
| 25 | 2-Bromo-5-fluoro | 254–256 |
| 26 | 3-Chloro-4-bromo | 261–263 |
| 27 | 2,5-Difluoro | 268–270 |
| 28 | 2-Bromo-4-chloro | 210–213 |
| 29 | 2-Chloro-5-bromo | 218–220 |

All of the compounds listed hereinabove form salts with various kinds of acids. Examples of salts which can be used as pharmaceuticals or in pharmaceutical compositions are salts with hydrochloric acid, hydrobromic acid, sulfuric acid, citric acid, malonic acid, tartaric acid, malic acid, maleic acid, fumaric acid, benzoic acid, salicyclic acid, cinnamic acid, methanesulfonic acid, benzenesulfonic acid, toluenesulfonic acid, nicotinic acid, and so forth. Compounds according to the present invention all exhibit strong, anti-inflammatory action.

In Table 2 below, carrageenin edema inhibition activity (for rats) of representative compounds of the present invention is illustrated:

TABLE 2

| No. of Compounds Used | Carrageenin Edema Inhibition (%) by administration of: | |
|---|---|---|
|  | 50 mg/kg i.p. | 100 mg/kg i.p. |
| 1 | 56.8 | 57.2 |
| 2 | 43.6 | 54.2 |
| 3 | 37.1 | 45.5 |
| 4 | 44.4 | 49.3 |
| 5 | 41.9 | 40.2 |
| 9 | 38.1 | 40.5 |
| 10 | 53.8 | 56.1 |
| 11 | 49.0 | 47.1 |
| 13 | 40.9 | 49.2 |
| 15 | 43.2 | 54.5 |
| 19 | 34.2 | 47.8 |
| 20 | 42.7 | 50.8 |
| 21 | 35.6 | 40.6 |
| 24 | 46.5 | 45.1 |
| 25 | 40.7 | 45.9 |
| 27 | 51.2 | 53.6 |
| 28 | 42.8 | 48.4 |
| 29 | 38.7 | 49.2 |

In contrast, the unhalogenated compounds according to formula (I) wherein both X and Y are hydrogen exhibit inhibitory activity of not more than 28.3% and 40.3% by administration of 50 mg/kg and 100 mg/kg, respectively. Mono- and di-phenyl halogenated compounds, however, are characterized by significantly and statistically stronger inhibitory action at those same dosage levels as shown by Table 2.

Compounds of the present invention can be synthesized by various methods and the most readily and efficient method is by the reaction of a benzoguanamine having various halogeno substituent(s) with activated derivatives of nicotinic acid. As activated derivatives of nicotinic acid are various sulfonic acid anhydrides, such as dichlorophosphoric acid anhydride, alkylcarbonic acid anhydride, etc., and conventional acid anhydrides and acid chlorides. The methods may also be carried out in such manner that the activated nicotinic acid derivatives are caused to react with an excess of nicotinic acid and the resulting nicotinic acid anhydride formed is then reacted with a benzoguanamine.

Benzoguanamine compounds according to formula (I) have two amino groups therein and, when a nearly equimolar amount of activated nicotinic acid is used in the reaction, mononicotinoyl compounds are obtained as the main reaction product. When the reaction is conducted with the use of an excess of nicotinic acid reagent, then dinicotinoyl compounds are obtained in high yield. Such dinicotinoyl compounds can be readily converted to mononicotinoyl compounds by treatment with ammonia or various primary or secondary amines and the compounds of this invention can be similarly synthesized in such manner. An alternative method by which 2-amino-4-chloro-6-halophenyl-s-triazines are reacted with nicotinamide alkali metal salts can be advantageously used here also. In that case, the following modified method is followed by reacting a 2,4-dichloro-6-halophenyl-s-triazine and 2 moles of a nicotinamide alkali metal salt and the resulting dinicotinoyl compound is subjected to the afore-mentioned aminolysis.

By way of the following additional examples, synthesis of representative compounds of the present invention are illustrated:

EXAMPLE 1

Synthesis of the compound of Table 1.

A mixture of 2.0 grams of 2,4-diamino-6-p-chlorophenyl-s-triazine having a melting point of 249° to 252° C. and 2.2 grams of nicotinic acid anhydride is heated to reflux with stirring for two hours. After cooling the reaction solution, the resulting insoluble crystals are collected by filtration and washed with methanol and then with hot dioxane. Melting point of the product is 266° to 268° C. Yield 2.11 grams.

By the use of the halobenzoguanamines listed hereinbelow, the corresponding N-mononicotinoyl derivatives can be synthesized by the same procedure described above.

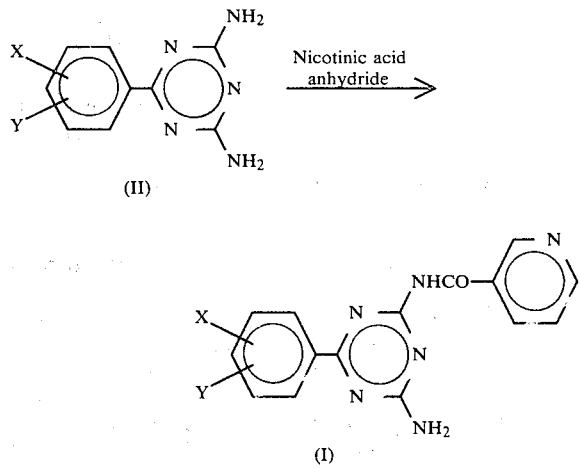

TABLE 3

| | Melting Points of Starting Materials (II) | |
|---|---|---|
| X and Y | Melting Points (°C.) | Resulting Compounds Therefrom |
| 2-Chloro | 227–229 | 3 |
| 4-Bromo | 264–265 | 4 |
| 3-Bromo | 231–233 | 5 |
| 2-Bromo | 247–248 | 6 |
| 4-Iodo | 262–264 | 7 |
| 3-Iodo | 251–254 | 8 |
| 2-Iodo | 256–259 | 9 |
| 3-Fluoro | 252–254 | 11 |
| 2-Fluoro | 247–249 | 12 |
| 2,4-Dichloro | 201–203 | 14 |
| 3,5-Dichloro | higher than 300 | 16 |
| 2,6-Dichloro | 270–277 | 17 |
| 2,3-Dichloro | 240–242 | 18 |
| 2-Fluoro-5-chloro | 249–250 | 19 |
| 2-Fluoro-4-chloro | 303–307 | 20 |
| 2,5-Dibromo | 273–274 | 21 |
| 2-Bromo-5-chloro | 262–263 | 22 |
| 2-Fluoro-5-bromo | 269–272 | 23 |
| 2-Chloro-5-fluoro | 215–216 | 24 |
| 2-Bromo-5-fluoro | 220–225 | 25 |
| 3-Chloro-4-bromo | 269–272 | 26 |
| 2,5-Difluoro | 241–243 | 27 |
| 2-Bromo-4-chloro | 215–216 | 28 |
| 2-Chloro-5-bromo | 281–282 | 29 |

EXAMPLE 2

Synthesis of compound 1 (alternative method)

Nicotinamide (1.5 grams) is dissolved in 50 ml. of anhydrous dioxane, 0.6 gram of sodium hydride is added thereto, and the mixture is heated to reflux with stirring for 30 minutes. After the reaction solution is cooled to room temperature, 2.4 grams of 2-amino-4-chloro-6-p-chlorophenyl-s-triazine (m.p. 273°–275° C.) is added thereto, and the mixture is stirred with warming for four hours. The reaction solution is cooled, insoluble matter is collected by filtration, washed with water and then with methanol and recrystallized from dioxane. Melting point 265°–268° C. Yield 2.51 grams.

The same procedure described above is carried out using 2-amino-4-chloro-6-m-chlorophenyl-s-triazine (m.p. 192°–194° C.), 2-amino-4-chloro-6-(3,4-dichlorophenyl)-s-triazine (m.p. 249°–150° C.) or 2-amino-4-chloro-6-(2,5-dichlorophenyl)-s-triazine to give the compounds 2, 13 or 15, respectively.

EXAMPLE 3

Synthesis of compound 1 (further modified method)

2,4-Diamino-6-p-chlorophenyl-s-triazine (2.21 grams) and nicotinic acid (1.5 grams) are added to 30 ml. of pyridine and then 2.0 grams of phosphorous oxychloride is added thereto at a time with ice cooling and stirring. The mixture is heated with stirring at 70° to 80° C. for one hour, evaporated in vacuo to dryness, water is added to the residue, insoluble matter is collected by filtration, washed with methanol and recrystallized from a mixture of dioxane and isopropanol (1:1). Melting point of the product is 267° to 268° C. Yield 1.98 grams.

EXAMPLE 4

Synthesis of the compound 10

Nicotinic acid (7.0 grams) is dissolved in 150 ml. of pyridine, 3.5 grams of methanesulfonic acid chloride is added thereto, and the mixture is heated to reflux for 30 minutes. Then 4.9 grams of 2,4-diamino-6-p-fluorophenyl-s-triazine (m.p. 280° to 283° C.) is added and the mixture is heated to reflux with stirring for three hours. After the reaction, the mixture is concentrated in vacuo, water is added to the concentrate, the insoluble matter is collected by filtration, dissolved in 300 ml. of methanol, heated to reflux for two hours with stirring, concentrated and the resulting crystals are collected by filtration. Melting point of the product 257° to 260° C. Yield 4.13 grams.

EXAMPLE 5

Synthesis of compound 2

2,4-Diamino-6-m-chlorophenyl-s-triazine (2.2 grams) and 3.0 grams of nicotinic acid are added to 100 ml. of pyridine and 2.6 grams of methanesulfonyl chloride is dropped thereinto during ten minutes with stirring and refluxing. After the dropping procedure, the mixture is heated to reflux for four hours. The reaction mixture is concentrated in vacuo and evaporated to dryness, water is added to the residue, insoluble matter is collected therefrom by filtration and washed with water, methanol and hot dioxane in that order. The compound thereby obtained is 2,4-binicotinoylamino-6-m-chlorophenyl-s-triazine, melting point 253° to 256° C. Yield 3.81 grams.

The resulting binicotinoyl compound (3.80 grams) is suspended in 100 ml. of dioxane and the suspension is stirred for four hours with 30 ml. of 28% ammonia water at 20° to 25° C. After the reaction which occurs, the reaction solution is concentrated in vacuo at below 40° C., water is added to the concentrate, insoluble matter is collected therefrom by filtration and recrystallized from a mixture of dioxane and methanol (1:1). Melting point of the product is 260° to 262° C. Yield 1.75 grams.

Anti-inflammatory compounds and their acid addition salts according to the invention may be formulated as pharmaceutical compositions with the usual or conventional pharmaceutically acceptable excipients or carriers and the compositions may be formed into dosage units in any suitable or known manner, as by tabletting or introduction in gelatin capsules, or made up as liquids or elixirs, as desired, and the compositions may be administered to treat human or animal hosts having inflammatory conditions or disorders. The dosage administered is that determined by a physician, clinician or other technician and may be continued until the inflammation is reduced or overcome. The compounds have no known objectionable toxicity or contra-indications. The effective dosage used is adjusted in known manner to the severity of the inflammatory condition. Usually, the oral dosage for humans is preferably in the range of 100 to 1,500 mg/day and, more preferably, in the range of 100 to 800 mg/day.

What is claimed is:

1. A nicotinoylbenzoguanamine derivative or an acid addition salt thereof of the formula (I):

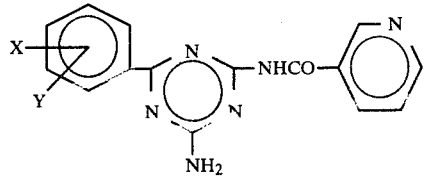

in which X and Y are the same or different and each independently is hydrogen or halogen, but both X and Y are not simultaneously hydrogen.

2. A compound of claim 1 in which X is hydrogen and Y is fluorine.
3. A compound of claim 1 in which X is hydrogen and Y is chlorine.
4. A compound of claim 1 in which X is hydrogen and Y is bromine.
5. A compound of claim 1 in which X is hydrogen and Y is iodine.
6. A compound of claim 1 in which X is fluorine and Y is chlorine.
7. A compound of claim 1 in which X is chlorine and Y is bromine.
8. A compound of claim 1 in which X is fluorine and Y is bromine.
9. A compound of claim 1 in which both X and Y are fluorine.
10. A compound of claim 1 in which both X and Y are chlorine.
11. A compound of claim 1 in which both X and Y are bromine.
12. An acid addition salt of a compound of claim 1 in which the salt-forming moiety is hydrochloric acid, hydrobromic acid, sulfuric acid, citric acid, malonic acid, tartaric acid, malic acid, maleic acid, fumaric acid, benzoic acid, salicylic acid, cinnamic acid, methanesulfonic acid, benzenesulfonic acid, toluenesulfonic acid or nicotinic acid.
13. A compound of claim 1 which is a 2-amino-4-nicotinoyl-amino-6-halogenophenyl-s-triazine or an acid addition salt thereof.
14. A compound according to claim 13 in which the halogenophenyl part is mono- or di-halogenophenyl.
15. An anti-inflammatory pharmaceutical composition comprising an anti-inflammatory effective amount of a compound of claim 1 and a pharmaceutically acceptable excipient or carrier.
16. An anti-inflammatory pharmaceutical composition comprising an anti-inflammatory effective amount of a compound of claim 1 and a pharmaceutically acceptable excipient or carrier in bulk or dosage form.
17. An anti-inflammatory pharmaceutical composition comprising an anti-inflammatory effective amount of a compound of claim 1 and a pharmaceutically acceptable excipient or carrier wherein the compound is a 2-amino-4-nicotinoylamino-6-halogenophenyl-s-triazine in which the halogenophenyl part is mono- or di-substituted by halogen.
18. A method of treating humans and animals suffering from inflammatory conditions and disorders which comprises administering to such humans and animals an anti-inflammatory amount of a composition of claim 15.
19. A method of treating humans and animals suffering from inflammatory conditions and disorders which comprises administering to such humans and animals an anti-inflammatory amount of a composition of claim 17.
20. A method of synthesizing a compound of claim 1 which comprises reacting a benzoguanamine which is halogeno-substituted with an active derivative of nicotinic acid and recovering the 2-amino-4-nicotinoylamino-6-halogenophenyl-s-triazine thus formed.

* * * * *